(12) United States Patent
Bussu

(10) Patent No.: US 7,581,457 B2
(45) Date of Patent: Sep. 1, 2009

(54) METHOD AND APPARATUS FOR TESTING MATERIALS

(75) Inventor: Giancarlo Bussu, Wassenaar (NL)

(73) Assignee: Agence Spatiale Europeenne, Paris Cedex (FR)

( * ) Notice: Subject to any disclaimer, the term of this patent is extended or adjusted under 35 U.S.C. 154(b) by 269 days.

(21) Appl. No.: 11/544,659

(22) Filed: Oct. 10, 2006

(65) Prior Publication Data
US 2007/0084303 A1   Apr. 19, 2007

(30) Foreign Application Priority Data
Oct. 12, 2005   (FR)   .................................. 05 10396

(51) Int. Cl.
*G01N 3/24*   (2006.01)
*G01N 17/00*   (2006.01)
*G01N 33/00*   (2006.01)

(52) U.S. Cl. .......................... 73/865.6; 73/841; 73/856; 422/53; 436/2; 436/5

(58) Field of Classification Search ................ 73/865.6, 73/866, 86, 788, 799, 841, 845, 856; 356/237.2; 422/53; 436/2, 5–6
See application file for complete search history.

(56) References Cited

U.S. PATENT DOCUMENTS

| | | | | |
|---|---|---|---|---|
| 2,923,148 | A | * | 2/1960 | Kirkham et al. ................. 73/86 |
| 3,216,238 | A | * | 11/1965 | Bailey .............................. 73/7 |
| 3,488,681 | A | * | 1/1970 | Masakatsu et al. ...... 73/865.6 X |
| 4,799,390 | A | * | 1/1989 | Kimura ...................... 73/865.6 |
| 5,182,955 | A | * | 2/1993 | Minette ...................... 73/865.6 |
| 5,945,594 | A | * | 8/1999 | Kendig et al. .................. 73/86 |
| 5,987,961 | A | * | 11/1999 | Harris et al. .............. 73/866 X |
| 6,131,443 | A | * | 10/2000 | Duncan .......................... 73/86 |

(Continued)

FOREIGN PATENT DOCUMENTS

EP   0195735   9/1986   .................. 73/760

(Continued)

OTHER PUBLICATIONS

G.Bussu et al., "Experimental Assessment of the Susceptibility to Stress-Corrosion Cracking of Ti-6Al-4V Alloy Exposed to Mon-1 Propellant Tank Environment—Background and Test Design", 4th Int. Spacecraft Propulsion Conference, Jun. 2-4, 2004, pp. 1-7.

*Primary Examiner*—Thomas P Noland
(74) *Attorney, Agent, or Firm*—Clark & Brody

(57) ABSTRACT

An apparatus for performing tests on materials, the apparatus comprising a leaktight receptacle defining an inside volume, the receptacle being provided with an opening and the ability to provide leaktight contact between the edges of the opening and a portion of a surface of a test piece of a material disposed outside the receptacle. The receptacle also has the ability for introducing at least one chemical agent in order to create, within the inside volume, a test chemical environment to which the surface portion of the test piece is exposed; and with a drain for draining the introduced chemical agent(s). The receptacle is also provided with a bottom including a surface that is inclined or conical and that co-operates with the drain to enable the introduced chemical agent(s) to be removed totally or in part. The apparatus is used in a method for carrying out tests on materials.

24 Claims, 2 Drawing Sheets

U.S. PATENT DOCUMENTS 6,156,267 A * 12/2000 Pai et al. .................... 422/3
6,762,056 B1 * 7/2004 Peeters ..................... 436/86
6,799,471 B1 * 10/2004 Regimand et al. ...... 73/865.6 X

FOREIGN PATENT DOCUMENTS

| | | | |
|---|---|---|---|
| FR | 2346709 | 10/1977 | |
| JP | 60-061644 | 4/1985 | ............ 73/86 |
| JP | 04190139 A * | 7/1992 | ............ 73/760 |
| JP | 06273592 A * | 9/1994 | |
| JP | 08-005532 | 1/1996 | |
| JP | 2002048705 A * | 2/2002 | |
| WO | WO 9729789 A1 * | 8/1997 | |

* cited by examiner

METHOD AND APPARATUS FOR TESTING MATERIALS

The invention relates to a method and apparatus for testing materials exposed to a determined chemical environment. In particular, the invention enables corrosion tests to be performed under stress.

BACKGROUND OF THE INVENTION

Environmental testing of materials involves exposing a test piece of a material to a specific environment (chemical, thermal, etc.) in order to reveal any adverse effects of that environment on its properties, and in particular on its mechanical properties. When one of the properties of the material that needs to be analyzed is its ability to withstand propagation of an existing defect, e.g. a surface crack, it is necessary to be able to subject the test piece to mechanical stresses, e.g. in traction. Applying and varying stresses, and also observing propagation of the defect, require the test piece to be accessible during testing. This raises a problem when the test piece must simultaneously be exposed to a test environment that is corrosive, toxic, flammable, and/or likely to be contaminated.

In the prior art, it is known to carry out mechanical tests on a test piece placed inside a leaktight receptacle in which the desired test environment is created (e.g. the presence of corrosive vapor). That method makes it possible, in satisfactory manner, to control the physico-chemical characteristics of the test environment (pressure, temperature, chemical composition, . . . ), but it presents the drawback of making the test piece inaccessible throughout the duration of the test.

It is also known to carry out tests on a test piece in which a portion of its surface is exposed to a flow of a potentially corrosive composition in the liquid or gaseous state. In that way, the test piece can be accessible in part during the test, but the characteristics of its environment are difficult to control, and in general cannot faithfully reproduce the real conditions encountered on a mechanical part while it is in use. In addition, that approach is difficult to implement with compositions that are dangerous (toxic, flammable, explosive, . . . ) or that might be contaminated.

OBJECT AND SUMMARY OF THE INVENTION

There therefore exists a need for a method of testing that does not present the above-mentioned drawbacks of the prior art and for an apparatus enabling the method to be implemented.

In one aspect, the invention provides an apparatus for performing tests on materials, the apparatus comprising a leaktight receptacle defining an inside volume, said receptacle being provided with an opening and with means for providing leaktight contact between the edges of said opening and a portion of a surface of a test piece of a material disposed outside said receptacle.

In particular embodiments of the apparatus of the invention:
said receptacle is also provided with means for introducing at least one chemical agent in order to create, within said inside volume, a test chemical environment to which said surface portion of the test piece is exposed;
said receptacle is also provided with drain means for draining said introduced chemical agent(s);
said receptacle is also provided with a bottom including a surface that is inclined or conical and that co-operates with said drain means to enable said introduced chemical agent(s) to be removed totally or in part;
said receptacle is also provided with retaining means for retaining a predetermined quantity of said or each introduced chemical agent, said means comprising for example a groove or a pit formed in the bottom of said receptacle;
the apparatus may include means for optically inspecting said surface portion of the test piece that is exposed to said test chemical environment;
the apparatus may include means for applying mechanical stress to said test piece, said means being situated outside said receptacle, and more particularly means for applying a traction stress in a direction parallel to said surface portion of the test piece that is exposed to said test chemical environment; and
the means for providing leaktight contact between the edges of said opening and a portion of a surface of a test piece include an element for reducing friction between said means and said test piece.

In another aspect, the invention provides a method of performing tests on materials, the method comprising the following steps:
forming leaktight contact between the edges of an opening formed in a leaktight receptacle and a portion of a surface of a test piece of a material, said test piece remaining outside said receptacle;
introducing into said receptacle at least one chemical agent so as to create inside said receptacle a test chemical environment to which said surface portion of the test piece is exposed; and
applying mechanical stress to said test piece with the help of means situated outside said receptacle.

In particular implementations of the method of the invention:
said mechanical stress may comprise traction stress in a direction parallel to said surface portion of the test piece that is exposed to said test chemical environment;
said test chemical environment may be an environment that is corrosive for said material and said test may be corrosion tests under stress; and
at least one chemical agent introduced into said receptacle may be in the liquid or the solid state, and the method may also comprise, after the step of introducing said chemical agent, draining part of the agent away so as to leave only a predetermined quantity inside said receptacle. The predetermined quantity may or may not be in direct contact with said surface portion of the test piece. At least partial evaporation of said predetermined quantity may be implemented. In a variant, still after the step of introducing said chemical agent, the method may include draining all of the agent away so as to leave only vapor inside said receptacle.

BRIEF DESCRIPTION OF THE DRAWINGS

Other characteristics, details, and advantages of the invention appear on reading the following description made with reference to the accompanying drawings that are given by way of example and that show, respectively.

MORE DETAILED DESCRIPTION

Figure 1:
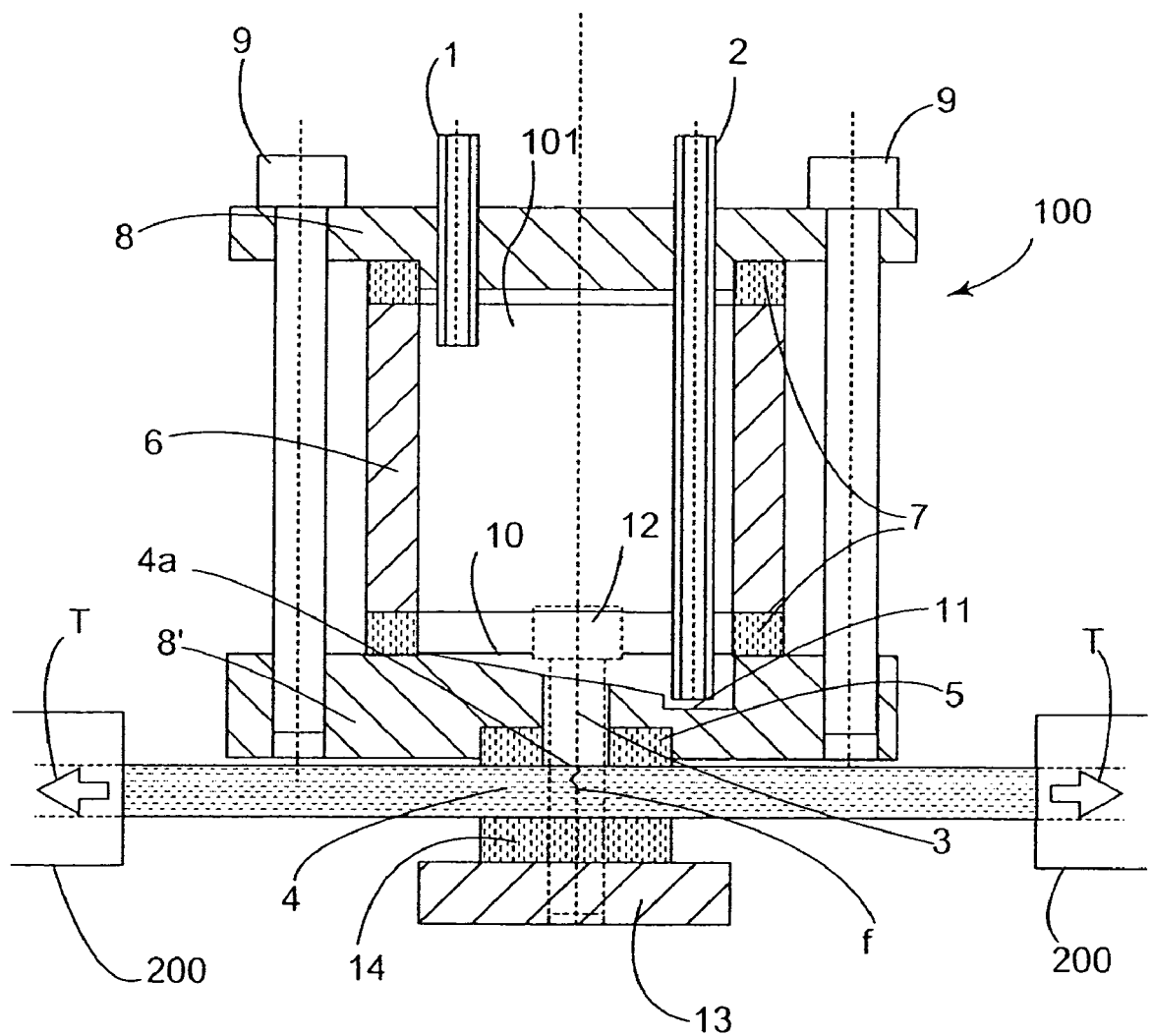
FIG. 1 a section view of apparatus constituting a first embodiment of the invention.

The apparatus of FIG. 1 comprises a leaktight receptacle 100 fitted with an admission pipe 1, a drain pipe 2, and an opening 3 for putting a surface portion 4a of a test piece 4 into communication with the inside volume 101 of the receptacle 100. In the embodiment described here, the receptacle 100 is constituted by a glass tube 6 (e.g. made of Pyrex glass) closed at its ends by two metal plates 8, 8' that are held in place by clamping screws 9. In use, the receptacle is held in a vertical position with the plate 8 (referred to as the top plate) on top, and with the plate 8' (referred to as the bottom plate) at the bottom. Organic gaskets 7, e.g. made of elastomer material, provide leaktight contact between the tube 6 and the plates 8, 8'.

The admission and drain pipes 1 and 2 pass through the top plate 8 and serve respectively to introduce and to remove chemical agents enabling the desired test environment to be created inside the receptacle 100; these agents may be supplied in the solid, liquid, or gaseous state. For reasons that become clear below, the apparatus shown in FIG. 1 is particularly well suited to using agents in the liquid state, possibly suitable for evaporating.

The opening 3 that serves to expose the surface portion 4a of the test piece 4 to the test environment is formed through the bottom plate 8', which constitutes the bottom of the receptacle 100. The shape of the outside face of the bottom plate 8' must be capable of fitting snugly to the shape of the test piece 4 so as to enable leaktight contact to be formed between the test piece and the edges of the opening 3. For example, if the test piece 4 presents a cross-section that is rectangular, said outside face may be plane; otherwise, if the test piece presents a section that is cylindrical, the outside face of the plate 8' needs to present a three-dimensional shape that presents, at least in register with the opening 3, curvature that matches the curvature of the surface of the test piece 4.

The bottom plate 8' presents an inside surface 10 that is plane and inclined, and at the bottom end of said surface 10 it presents a blind hole or pit 11 into which one end of the drain pipe 2 dips.

Screws 12 enable the test piece 4 to be clamped between a bearing plate 13 and the outside surface of the bottom plate 8' in such a manner that the surface portion 4a forms leaktight contact with the edges of the opening 3, which opening is provided with an organic sealing gasket 5. It is advantageous to interpose an element 14 made of organic material between the bearing plate 13 and the test piece 4 in order to reduce friction between these two elements, given that friction could disturb the distribution within the material of the mechanical stresses that are applied to the test piece 4 while carrying out a test. The element 14 is preferably of a shape that matches that of the test piece (e.g. plane for a test piece that is flat or of rectangular section), and it may be made of a material such as polytetrafluoroethylene (PTFE).

In order to carry out a corrosion test under stress, a test piece 4, generally of elongate shape, is initially secured between the bottom plate 8' of the receptacle 100 and the bearing plate 13 as mentioned above, taking care to keep said receptacle 100 in a vertical position. The ends of the test piece 4 are inserted in retention elements 201, 202 of a device 200 for applying mechanical stresses, e.g. a traction device. Thereafter, one or more liquid agents constituting a corrosive test environment are introduced into the receptacle 100 via the admission pipe 1. The liquid agents flow along the inclined plane surface 10 and fill the opening 3 which forms a well whose bottom is constituted by the surface portion 4a, and fills the blind hole or pit 11 into which the drain pipe 2 dips. Said drain pipe 2 is used subsequently for removing said liquid agents, with the exception of a predetermined quantity contained in the opening 3. At this point, the traction device 200 is actuated in order to perform a test under simple traction (arrows T in FIG. 1), during which the surface portion 4a remains exposed to the corrosive liquid agents, until the test piece breaks because of the growth in a surface crack f (possibly a pre-existing crack) under the combined effects of mechanical stress and of corrosion. Throughout the duration of the test, the test piece 4 remains accessible, with the exception of the surface 4a, since the test piece remains outside the receptacle 100, and the test environment is kept confined inside said receptacle 100, thus making it possible to monitor the properties of the test piece finely and to avoid any contamination. In addition, the transparency of the tube 6 makes it possible to inspect growth of the crack f optically.

This embodiment enables a desired volume of liquid agent to be maintained in the opening 3 where it is in direct contact with the surface 4a and where it can evaporate under static conditions. This is particularly advantageous when simulating specific environments such as a fuel tank from which residues are removed by evaporation after the tank has been emptied.

Figure 2:
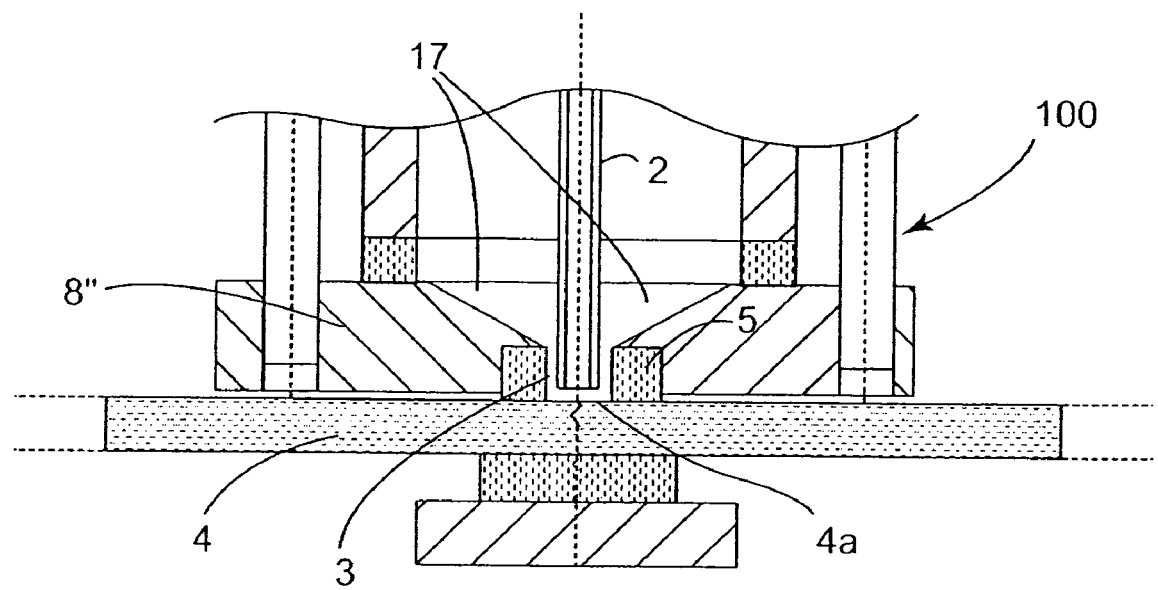
FIGS. 2 and 3 details of apparatus constituting second and third embodiments, respectively.

Under certain conditions, it can be desirable that the test piece 4 does not remain wetted by a corrosive liquid, since it is the effects of exposure to vapor that are of greatest interest. The apparatus of the invention can be adapted to such novel test conditions merely by replacing the bottom plate 8' with a modified plate 8'' as shown in FIG. 2. The inside surface 17 of the plate 8'' is in the form of a funnel that converges towards the exposure opening 3, and the drain pipe 2 dips into this opening. In this way, the liquid agents introduced by the admission pipe accumulate in said opening 3 and evaporate in part. The fraction of liquid that does not evaporate is removed in its entirety by the drain pipe 2: in this way, the surface portion 4a remains dry and exposed to vapor only.

Figure 3:
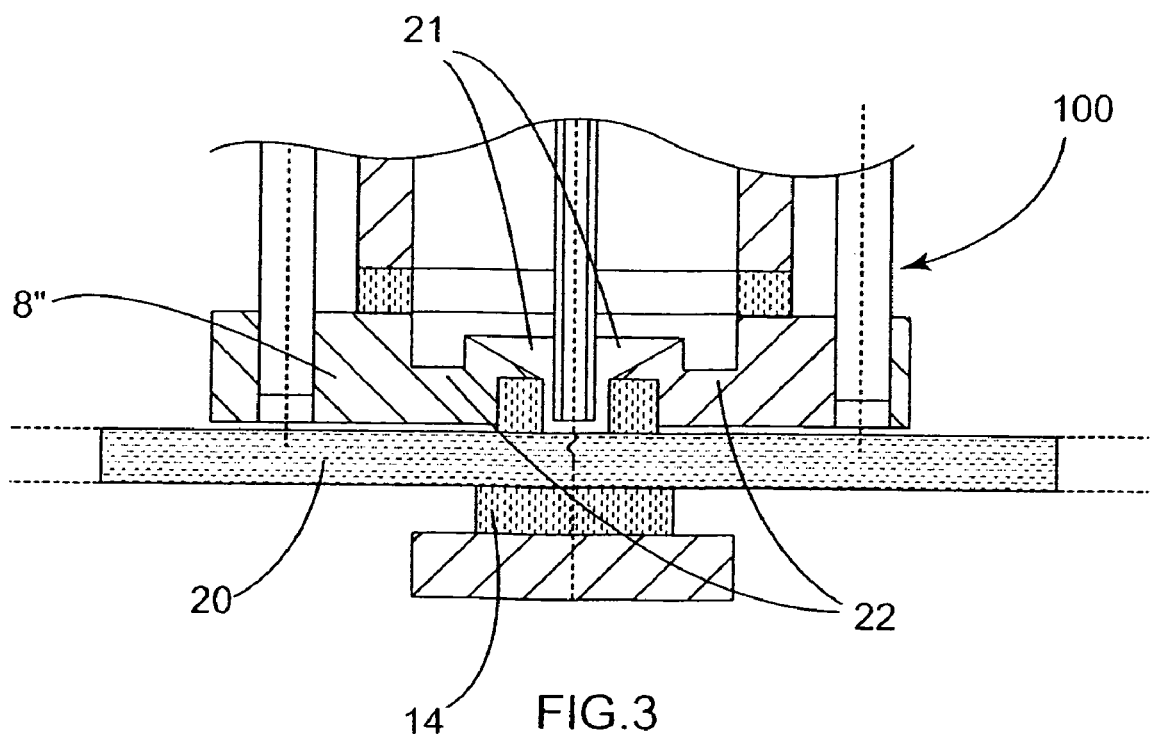

In a variant, as shown in FIG. 3, the bottom plate 8''' presents a circular groove 22 surrounding a funnel-shaped inside surface 21 that converges towards the exposure opening 3, in which one end of the drain pipe 2 dips. In this way, said drain pipe 2 does not remove the liquid agents in full, since said groove 22 retains a predetermined quantity thereof, which quantity evaporates under static conditions. This makes it possible, for example, to simulate the conditions that are to be encountered in an empty tank in which residues of content remain trapped in folds or crannies.

Under such circumstances, it should be observed that it is also possible to introduce a controlled quantity of liquid agents directly into the groove 22 alone so that the test piece 4 never comes into direct contact with those agents, i.e. so that it is never wetted.

The person skilled in the art will understand that all of the materials used must be compatible with the test environment that needs to be created for a specific application. Nevertheless, since the screws 9 compress the tube 6, there is a need for the material constituting the tube to present a high level of resistance to cracking due to corrosion under stress. In certain particular applications, it is not possible to use organic sealing gaskets.

Numerous variants of the method and the apparatus can be envisaged without going beyond the ambit of the present invention.

The above-described structure of the leaktight receptacle 100 is advantageous, but it does not constitute an essential element of the invention. For example, instead of a receptacle made of three portions (tube 6 and top plate 8 and bottom plates 8', 8'', or 8'''), it would be possible to use a receptacle made as a single piece, e.g. of glass.

The fact of using a glass tube 6 for making the side wall of the apparatus enables both the test environment and also the surface portion 4a to be inspected visually, however other visual inspection means could be provided, such as optical windows in an opaque wall, or even a camera in a structure that is entirely opaque.

Other shapes for the bottom wall 8', 8", 8''' can be envisaged, for example it could include one or more pits as means for retaining liquid agents.

The test environment can be created by introducing gas or vapor, or even solids suitable for subliming, into the receptacle 100, either instead of or in addition to the liquid agents described in the examples. In some circumstances, the drain pipe 2 may be omitted and/or the admission pipe 1 may be replaced by a simple orifice. Agents in the solid state can also be introduced into the receptacle 100 through the opening 3 prior to the opening being closed by the test piece 4: under such circumstances, both the admission pipe 1 and the drain pipe 2 may be omitted.

If liquids are not used for making the test environment, there is no need for the receptacle 100 to be maintained in a vertical position.

The receptacle 100 may also contain sensors for sensing temperature, pressure, humidity, chemical composition, etc. in order to obtain precise knowledge about the conditions in which tests are carried out. Heating and/or cooling means may also be provided.

The mechanical stresses applied by the device 200 are not restricted to simple traction as in the examples: on the contrary, the test piece 4 may be subjected to compression, twisting, or bending stresses, to vibration, etc., and this can be done without any need to modify the structure of the receptacle 100. This great flexibility in use constitutes one of the advantages of the invention compared with the prior art.

What is claimed is:

1. An apparatus for performing tests on materials, the apparatus comprising a leaktight receptacle defining an inside volume, said receptacle being provided:
   with an opening;
   with means for providing leaktight contact between the edges of said opening and a portion of a surface of a test piece of a material disposed outside said receptacle;
   with means for introducing at least one chemical agent in order to create, within said inside volume, a test chemical environment to which said surface portion of the test piece is exposed;
   with drain means for draining said introduced chemical agent(s);
   with a bottom including a surface that is inclined or conical and that cooperates with said drain means to enable said introduced chemical agent(s) to be removed totally or in part; and
   including means for applying mechanical stress to said test piece, said means being situated outside said receptacle, wherein said means for applying mechanical stress comprise means for applying traction stress in a direction parallel to said surface portion of the test piece that is exposed to said test chemical environment.

2. An apparatus according to claim 1, in which said receptacle is also provided with retaining means for retaining a predetermined quantity of said or each introduced chemical agent.

3. An apparatus according to claim 2, in which said retaining means comprise a groove or a pit formed in the bottom of said receptacle.

4. An apparatus according to claim 2, in which said retaining means are adapted for keeping said predetermined quantity of said or each introduced chemical agent away from said portion of a surface of a test piece.

5. An apparatus according to claim 1, also including means for optically inspecting said surface portion of the test piece that is exposed to said test chemical environment.

6. A method of using an apparatus according to claim 1 for carrying out tests on materials, the method comprising the following steps:
   forming leaktight contact between the edges of an opening formed in the leaktight receptacle of said device and a portion of a surface of a test piece of a material, said test piece remaining outside said receptacle;
   introducing into said receptacle at least one chemical agent so as to create inside said receptacle a test chemical environment to which said surface portion of the test piece is exposed;
   after said step of introducing said chemical agent, draining at least part of the agent away; and
   applying mechanical stress to said test piece with the help of means situated outside said receptacle.

7. A method according to claim 6, in which said chemical agent is in the liquid state or in the solid state.

8. A method according to claim 6, including draining part of the agent away so as to leave only a predetermined quantity in direct contact with said surface portion of the test piece.

9. A method according to claim 6, in which said receptacle is also provided with retaining means for retaining a predetermined quantity of said or each introduced chemical agent and keeping it away from said portion of a surface of a test piece, the method including draining part of the agent away so as to leave only a predetermined quantity not in direct contact with said surface portion of the test piece.

10. A method according to claim 9, implementing at least partial evaporation of said predetermined quantity;

11. A method according to claim 6, including draining away said agent in full so as to leave only vapor inside said receptacle.

12. A method according to claim 6, in which said test chemical environment is a corrosive environment for said material and in which said tests are corrosion tests under stress.

13. A method of using an apparatus according to claim 6 for carrying out tests on materials, the method comprising the following steps:
   forming leaktight contact between the edges of an opening formed in the leaktight receptacle of said device and a portion of a surface of a test piece of a material, said test piece remaining outside said receptacle;
   introducing into said receptacle at least one chemical agent so as to create inside said receptacle a test chemical environment to which said surface portion of the test piece is exposed;
   after said step of introducing said chemical agent, draining at least part of the agent away; and
   applying mechanical stress to said test piece with the help of means situated outside said receptacle.

14. A method according to claim 13, in which said chemical agent is in the liquid state or in the solid state.

15. A method according to claim 13, including draining part of the agent away so as to leave only a predetermined quantity in direct contact with said surface portion of the test piece.

16. A method according to claim 13, in which said receptacle is also provided with retaining means for retaining a predetermined quantity of said or each introduced chemical agent and keeping it away from said portion of a surface of a test piece, the method including draining part of the agent away so as to leave only a predetermined quantity not in direct contact with said surface portion of the test piece.

17. A method according to claim 13, implementing at least partial evaporation of said predetermined quantity.

18. A method according to claim 13, including draining away said agent in full so as to leave only vapor inside said receptacle.

19. A method according to claim 13, in which said test chemical environment is a corrosive environment for said material and in which said tests are corrosion tests under stress.

20. An apparatus for performing tests on materials, the apparatus comprising a leaktight receptacle defining an inside volume, said receptacle being provided:
   with an opening;
   with means for providing leaktight contact between the edges of said opening and a portion of a surface of a test piece of a material disposed outside said receptacle;
   with means for introducing at least one chemical agent in order to create, within said inside volume, a test chemical environment to which said surface portion of the test piece is exposed;
   with drain means for draining said introduced chemical agent(s); and
   with a bottom including a surface that is inclined or conical and that cooperates with said drain means to enable said introduced chemical agent(s) to be removed totally or in part, in which the means for providing leaktight contact between the edges of said opening and a portion of a surface of a test piece include an element for reducing friction between said means and said test piece.

21. An apparatus according to claim 20, in which said receptacle is also provided with retaining means for retaining a predetermined quantity of said or each introduced chemical agent.

22. An apparatus according to claim 21, in which said retaining means comprise a groove or a pit formed in the bottom of said receptacle.

23. An apparatus according to claim 21, in which said retaining means are adapted for keeping said predetermined quantity of said or each introduced chemical agent away from said portion of a surface of a test piece.

24. An apparatus according to claim 20, also including means for optically inspecting said surface portion of the test piece that is exposed to said test chemical environment.

* * * * *